US00PP19645P2

(12) United States Plant Patent
Hooijman

(10) Patent No.: US PP19,645 P2
(45) Date of Patent: Jan. 20, 2009

(54) ***HYPERICUM* PLANT NAMED 'ESM ESPAÑOLA'**

(50) Latin Name: *Hypericum androsaemum*
Varietal Denomination: Esm Española

(75) Inventor: Aloysius A. J. Hooijman, Aalsmeer (NL)

(73) Assignee: ESmeralda Breeding B.V., Aalsmeer (NL)

( * ) Notice: Subject to any disclaimer, the term of this patent is extended or adjusted under 35 U.S.C. 154(b) by 4 days.

(21) Appl. No.: 11/700,682

(22) Filed: Jan. 30, 2007

(51) Int. Cl.
*A01H 5/00* (2006.01)

(52) U.S. Cl. ..... Plt./442
(58) Field of Classification Search ..... Plt./442
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of *Hypericum* plant named 'Esm Española', characterized by its upright and uniform plant habit; strong flowering stems; uniform and freely flowering habit; uniform and high density of fruits; large burgundy-colored fruits; and good postproduction longevity.

2 Drawing Sheets

Botanical designation: *Hypericum androsaemum.*
Cultivar denomination: 'Esm Española'.

BACKGROUND OF THE INVENTION

The present invention relates to a new and distinct cultivar of *Hypericum,* botanically known as *Hypericum androsaemum* and hereinafter referred to by the name 'Esm Española'.

The new *Hypericum* is a product of a planned breeding program conducted by the Inventor in El Quinche, Pichincha, Ecuador. The objective of the breeding program is to create new cut flower *Hypericum* cultivars with numerous attractive fruit coloration.

The new *Hypericum* originated from an open-pollination in July, 1999 in El Quinche, Pichincha, Ecuador of a proprietary selection of *Hypericum androsaemum* identified as code number 5, not patented, as the female, or seed parent with an unknown selection of *Hypericum androsaemum* as the male, or pollen, parent. The new *Hypericum* was discovered and selected by the Inventor as a single flowering plant within the progeny of the stated open-pollination in a controlled environment in El Quinche, Pichincha, Ecuador Asexual reproduction of the new cultivar by vegetative cuttings in El Quinche, Pichincha, Ecuador, since February, 2000, has shown that the unique features of this new *Hypericum* are stable and reproduced true to type in successive generations.

SUMMARY OF THE INVENTION

Plants of the cultivar Esm Española have not been observed under all possible environmental conditions. The phenotype may vary somewhat with variations in environment such as temperature and light intensity without, however, any variance in genotype.

The following traits have been repeatedly observed and are determined to be the unique characteristics of 'Esm Española'. These characteristics in combination distinguish 'Esm Española' as a new and distinct cultivar of *Hypericum:*

1. Upright and uniform plant habit.
2. Strong flowering stems.
3. Uniform and freely flowering habit; uniform and high density of fruits.
4. Large burgundy-colored fruits.
5. Good postproduction longevity.

Plants of the new *Hypericum* differ from plants of the female parent selection in the following characteristics:

1. Plants of the new *Hypericum* are shorter than and not as vigorous as plants of the female parent selection.
2. Plants of the new *Hypericum* differ from plants of the female parent selection in fruit color as plants of the female parent selection have brown-colored fruits.

Plants of the new *Hypericum* can be compared to plants of the cultivar Excellent Flair, not patented. In side-by-side comparisons conducted by the Inventor in El Quinche, Pichincha, Ecuador, plants of the new *Hypericum* differed from plants of the cultivar Excellent Flair in the following characteristics:

1. Plants of the new *Hypericum* were shorter, but broader than plants of the cultivar Excellent Flair.
2. Plants of the new *Hypericum* flowered one to two weeks earlier than plants of the cultivar Excellent Flair.
3. Plants of the new *Hypericum* and the cultivar Excellent Flair differed in fruit color as plants of the cultivar Excellent Flair had brownish red-colored fruits.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Hypericum.*

The photograph on the first sheet comprises a side perspective view of a typical flowering plant of 'Esm Española'.

The photograph on the second sheet comprises a side perspective view of a typical fruiting plant of 'Esm Española'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following description were grown under conditions which closely approximate commercial production conditions in an outdoor nursery in El Quinche, Pichincha, Ecuador for about 18 months. During the production of the plants, day temperatures ranged from 11° C. to 28° C., night temperatures ranged from 5° C. to averaged 11° C. and light levels ranged from 1,000 to 1,150 foot-candles.

Botanical classification: *Hypericum androsaemum* cultivar Esm Española.

Parentage:

*Female, or seed, parent.*—Proprietary selection of *Hypericum androsaemum* identified as code number 5, not patented.

*Male, or pollen, parent.*—Unknown selection of *Hypericum androsaemum.*

Propagation:

*Type cutting.*—Vegetative cuttings.

*Time to initiate roots.*—About seven to ten days at 22° C. to 30° C.

*Time to produce a rooted young plant.*—About four to five weeks at 22° C. to 30° C.

*Root description.*—Fine, fibrous; color, 200C.

*Rooting habit.*—Freely branching; moderately dense.

Plant description:

*Form.*—Upright plant form; narrow inverted triangle. Freely branching with about five flowering stems developing per plant per year; dense and bushy plant form; vigorous growth habit.

*Plant height.*—About 80 cm.

*Plant width (spread).*—About 35 cm.

*Lateral branch description.*—Length: About 70 cm. Diameter: About 6 mm. Internode length: About 6.4 cm. Strength: Strong. Texture: Smooth, glabrous. Color: 146C overlain with 182A.

Foliage description:

*Arrangement.*—Opposite, simple; sessile.

*Length.*—About 7.5 cm.

*Width.*—About 4.6 cm.

*Shape.*—Ovate.

*Apex.*—Acute.

*Base.*—Slightly cordate.

*Margin.*—Entire.

*Texture, upper and lower surfaces.*—Smooth, glabrous.

*Venation pattern.*—Pinnate.

*Color.*—Developing foliage, upper surface: Close to 137B. Developing foliage, lower surface: Close to 138D. Fully expanded foliage, upper surface: Close to 137A to 139A; venation, close to 145A, towards the base, close to 187B. Fully expanded foliage, lower surface: Close to 138B to 146B; venation, 147C.

Flower description:

*Flower arrangement and shape.*—Bright yellow-colored single flowers arranged in terminal compound umbels with about 15 flowers per umbel. Flowers not persistent. Flowers face mostly upright.

*Fragrance.*—Moderate.

*Natural flowering season.*—Summer, typically June to September in The Netherlands.

*Postproduction longevity.*—Cut flowers are typically harvested when all flowers have developed fruits. Postproduction longevity of cut stems with fruits is about nine days.

*Flower buds.*—Length: About 1.15 cm. Diameter: About 8 mm. Shape: Globose. Color: 13A.

*Inflorescence size.*—Length: About 12 cm. Diameter: About 11.4 cm.

*Flowers.*—Diameter: About 3.1 cm. Depth (height): About 1.9 cm.

*Petals.*—Quantity/arrangement: Five in a single whorl. Length: About 1.6 cm. Width: About 1 cm. Shape: Oval. Apex: Obtuse. Base: Attenuate. Margin: Entire. Texture, upper and lower surfaces: Glabrous, smooth. Color: When opening, upper surface: 14A. When opening, lower surface: 13B. Fully opened, upper surface: 12A; color becoming closer to 163B with development. Fully opened, lower surface: 12B.

*Sepals.*—Quantity/arrangement: Five in a single whorl. Length: About 1 cm. Width: About 8.6 mm. Shape: Ovate to round. Apex: Acute. Base: Attenuate. Margin: Entire. Texture, upper and lower surfaces: Glabrous, smooth. Color: When opening, upper surface: Close to 144B; towards the apex and base, 187C. When opening, lower surface: Close to 144C; towards the apex and base, 187C. Fully opened, upper surface: Close to 144A; towards the base, 187C. Fully opened, lower surface: Close to 143C.

*Peduncles.*—Strength: Strong. Length: About 5.4 cm. Diameter: About 4.2 mm. Texture: Smooth, glabrous. Color: 144B overlain with 183B.

*Pedicels.*—Strength: Strong. Length: About 1.4 cm. Diameter: About 1.8 mm. Aspect: About 39° from the stem axis. Texture: Smooth, glabrous. Color: 144A overlain with 177A.

*Reproductive organs.*—Stamens: Quantity per flower: About 101. Anther shape: Reniform. Anther length: About 1.2 mm. Anther color: Close to 15A. Pollen amount: Moderate. Pollen color: Close to 21A. Pistils: Quantity per flower: Three. Pistil length: About 1.6 cm. Stigma shape: Circular. Stigma color: Close to 183A. Style length: About 7.7 mm. Style color: Close to 154C. Ovary color: Close to 151B.

*Fruits.*—Length: About 1.8 cm Diameter: About 1.1 cm. Shape: Elliptic. Texture: Smooth, glabrous. Color: Close to 187B; towards the base, close to 53A.

*Seeds.*—Length: About 1 mm. Diameter: About 0.03 mm. Color: Close to 200C.

Disease/pest resistance: Plants of the new *Hypericum* have not been noted to be resistant to pathogens and pests common to *Hypericum.*

Temperature tolerance: Plants of the new *Hypericum* have been observed to tolerate temperatures ranging from about 0° C. to about 30° C.

It is claimed:

1. A new and distinct *Hypericum* plant named 'Esm Española' as illustrated and described.

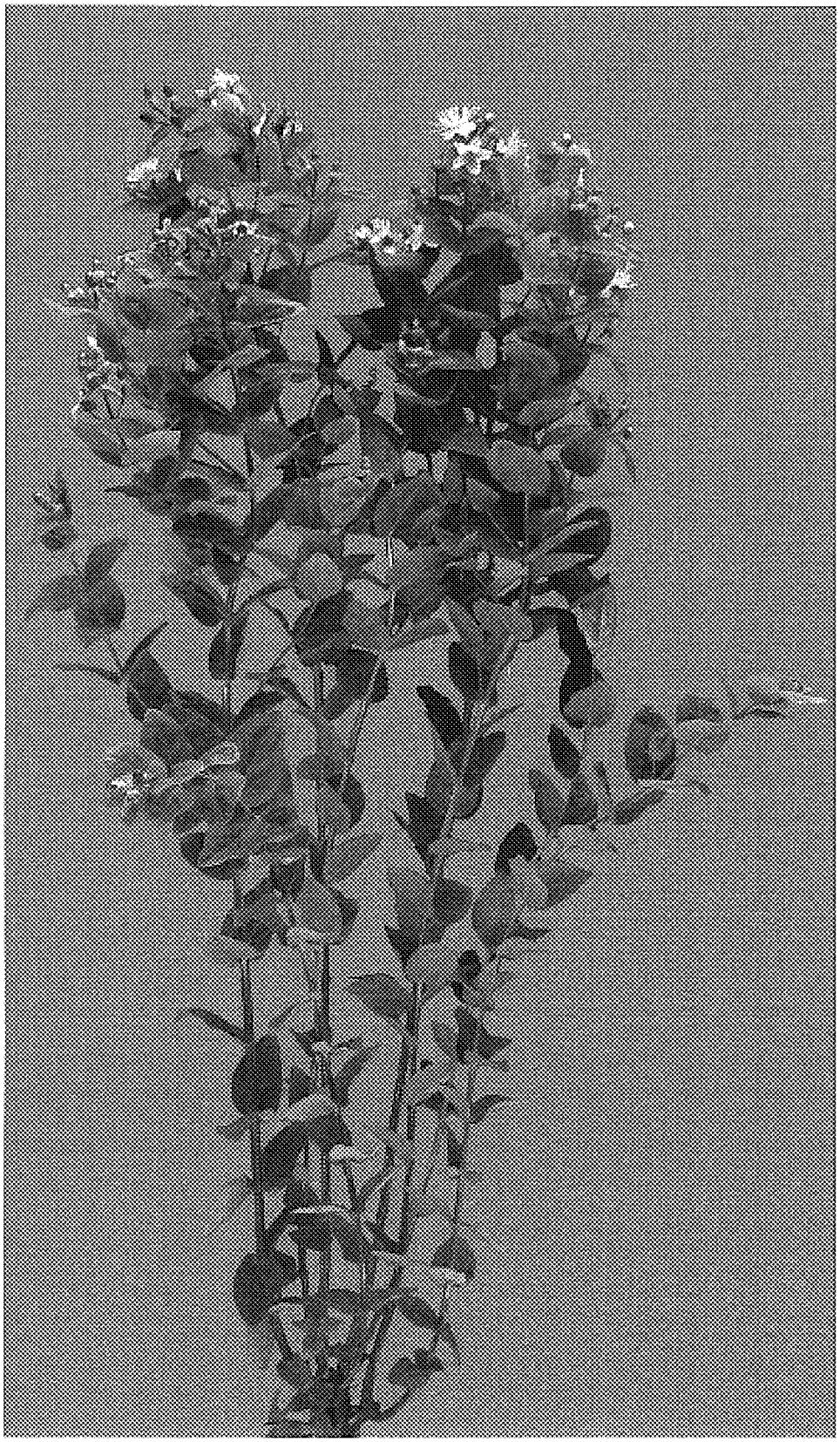

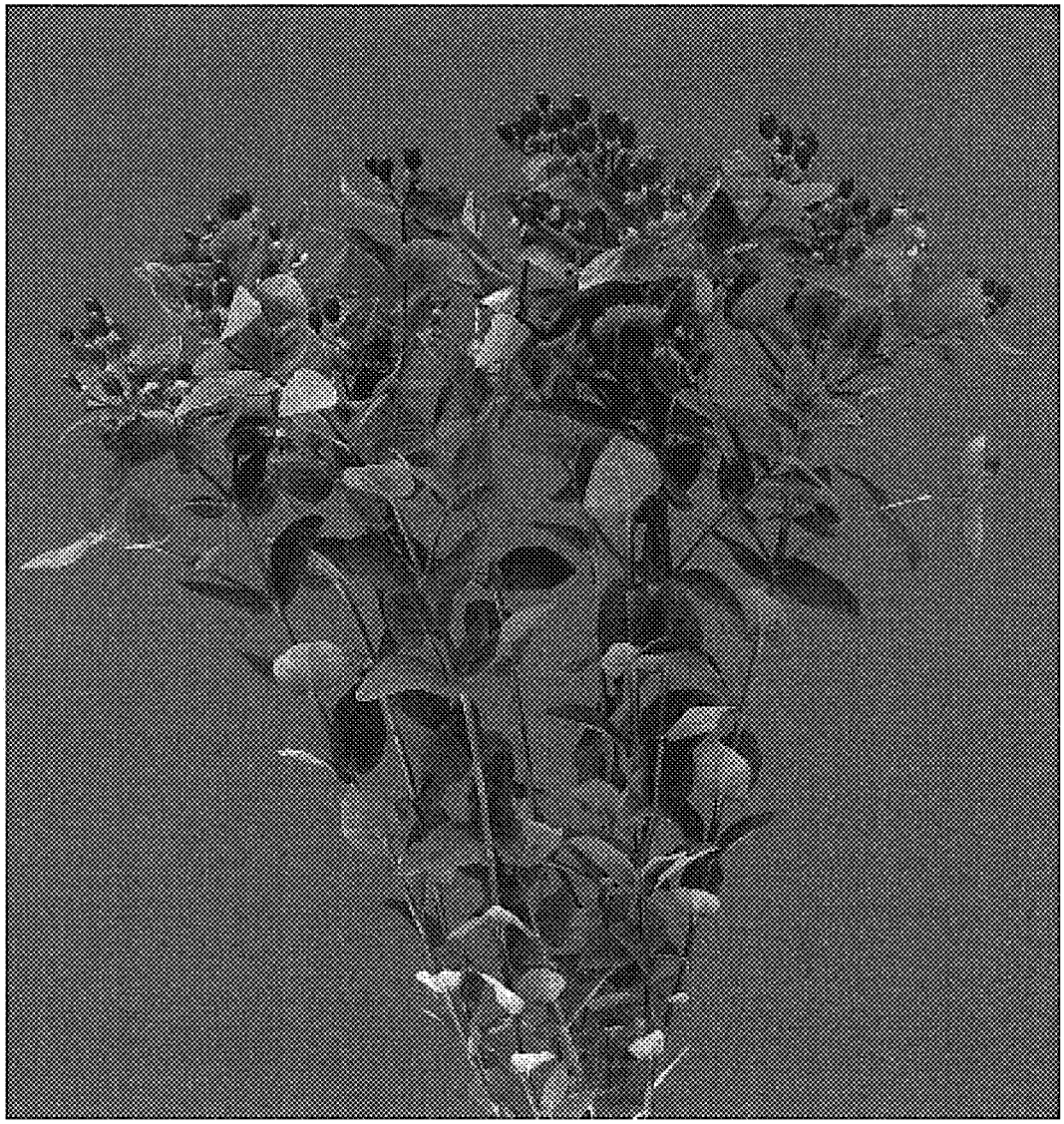

* * * * *